(12) United States Patent
Oliphant et al.

(10) Patent No.: US 7,075,064 B2
(45) Date of Patent: Jul. 11, 2006

(54) SYSTEM AND METHOD FOR EXTRACTING SPECTRA FROM DATA PRODUCED BY A SPECTROMETER

(75) Inventors: James R. Oliphant, Pleasant Grove, UT (US); H. Dennis Tolley, Mapleton, UT (US); Alan Rockwood, Provo, UT (US); Edgar Lee, Highland, UT (US); Milton Lee, Pleasant Grove, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 11/134,560

(22) Filed: May 20, 2005

(65) Prior Publication Data

US 2005/0258357 A1 Nov. 24, 2005

Related U.S. Application Data

(60) Provisional application No. 60/574,325, filed on May 24, 2004.

(51) Int. Cl.
*H01J 49/26* (2006.01)

(52) U.S. Cl. .......................... 250/281; 250/282; 702/26
(58) Field of Classification Search ................ 250/281, 250/282; 702/23, 24, 26
See application file for complete search history.

(56) References Cited

U.S. PATENT DOCUMENTS

2002/0138210 A1 * 9/2002 Wilkes et al. ............... 702/28

* cited by examiner

*Primary Examiner*—Kiet T. Nguyen
(74) *Attorney, Agent, or Firm*—Thorpe North & Western LLP

(57) ABSTRACT

A system and method are provided of extracting spectra from data produced by temporally indexed spectral scans from a spectrometer and spectrometer. The method includes the operation of receiving a data matrix from the spectrometer. The noise can then be removed from the data matrix. A further operation is identifying spectra of interest in the data matrix based on information content. In addition, a reduction transformation can be applied to the data matrix based upon the spectra of interest based upon the denizen transformation for the purpose of extracting the spectra of interest from the data matrix.

23 Claims, 6 Drawing Sheets

SYSTEM AND METHOD FOR EXTRACTING SPECTRA FROM DATA PRODUCED BY A SPECTROMETER

This application claims priority to U.S. Provisional Patent Application Ser. No. 60/574,325 filed on May 24, 2004.

FIELD OF THE INVENTION

The present invention relates generally to spectroscopy.

BACKGROUND

While there are various devices designed for chemical analysis, one of the more widely used systems involves a physical separation using a chromatograph followed by a mass spectrometer. Various types of mass spectrometers are known which use a mass analyzer and incorporate a time-to-digital converter also known as an ion arrival counter. Time-to-digital converters are used, for example, in time of flight mass analyzers where packets of ions are ejected into a field-free drift region with essentially the same kinetic energy. In the drift region, ions with different mass-to-charge ratios in each packet of ions travel with different velocities and therefore arrive at an ion detector disposed at the exit of the drift region at different times. Measurement of the ion transit-time therefore determines the mass-to-charge ratio of that particular ion.

Currently, one of the more commonly employed ion detectors in time of flight mass spectrometers is a single ion counting detector in which an ion impacting a detecting surface produces a pulse of electrons by means of, for example, an electron multiplier. The pulse of electrons is typically amplified by an amplifier and a resultant electrical signal is produced. The electrical signal produced by the amplifier is used to determine the transit time of the ion striking the detector by means of a time to digital converter which is started once a packet of ions is first accelerated into the drift region. The ion detector and associated circuitry is therefore able to detect a single ion impacting onto the detector.

While many types of mass spectrometers can be used in analyzing compounds, all of these devices produce an extensive data matrix representing the mass spectra that have been measured using the mass spectrometer. These large data matrices can then be analyzed to determine which types of compounds are represented in a particular data matrix output.

The process of reducing a large set of continuously evolving spectra into individual constituent spectra has been addressed using various techniques. Some are based on good laboratory principles, others follow machine learning pathways.

Much has been written and many algorithms have been developed to tackle this problem of converting the spectral output by mass spectrometers into identifiable compounds. The most widely accepted of these has been offered as a complete program called AMDIS. This program is freely available from http://chemdata.nist.gov/mass-spc/amdis/overview.html. AMDIS is based on the automation of good laboratory techniques and the matching of patterns against a large library of compound patterns. However AMDIS is very compute intensive and relatively time consuming. Other algorithms approach the problem using machine learning which has similar drawbacks.

SUMMARY OF THE INVENTION

A system and method are provided for extracting spectra from data produced by temporally indexed spectral scans from a spectrometer. The method includes the operation of receiving a data matrix from the spectrometer. The noise can then be removed from the data matrix. A further operation is identifying spectra of interest in the data matrix based on information content. In addition, a reduction transformation can be applied to the data matrix based upon the denizen transformation for the purpose of extracting the spectra of interest from the data matrix.

Additional features and advantages of the invention will be apparent from the detailed description which follows, taken in conjunction with the accompanying drawings, which together illustrate, by way of example, features of the invention.

DETAILED DESCRIPTION

Figure 1A:
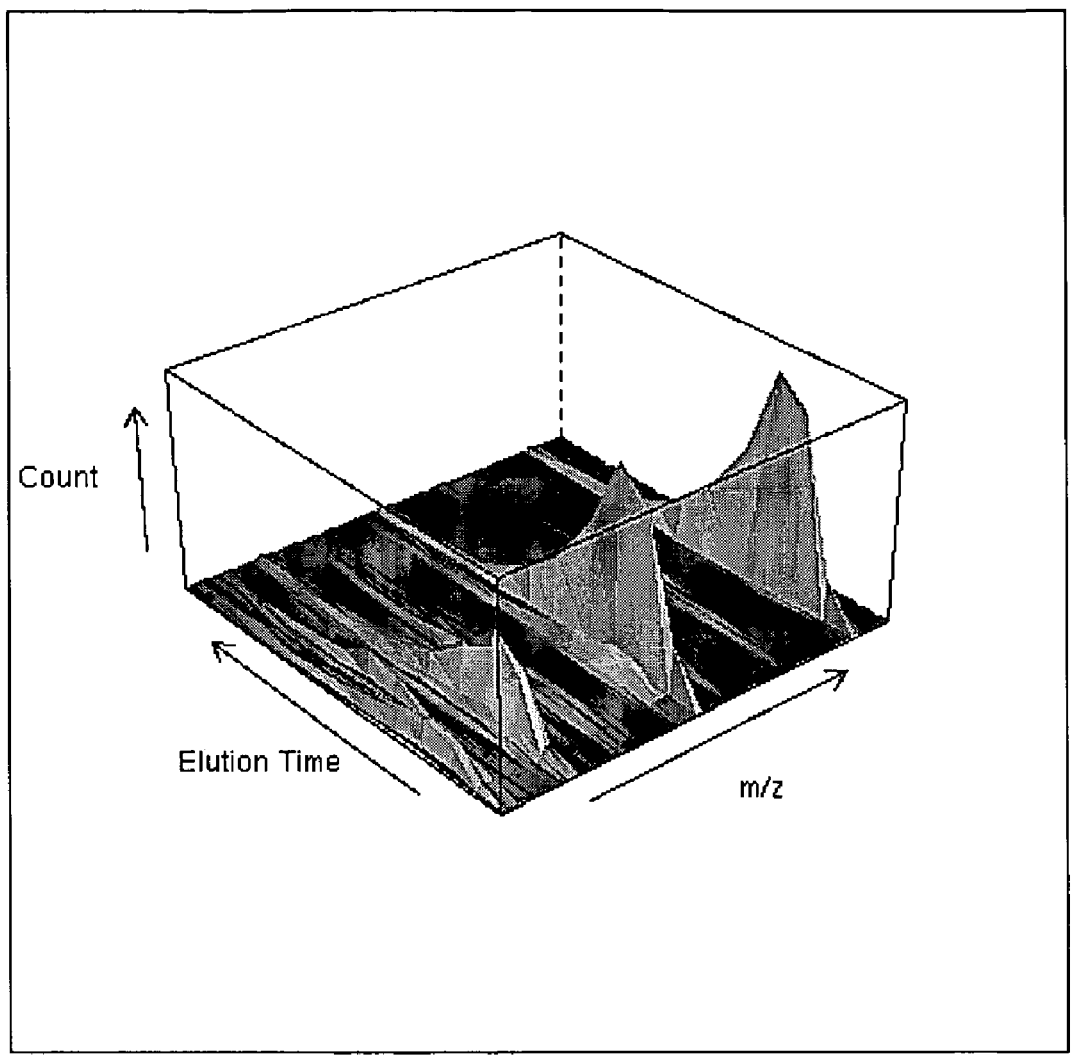
FIG. 1a illustrates an example data matrix produced by a spectrometer in an embodiment of the invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

A system and method is provided based on a transformation referred to herein as the denizen transformation, which may extract an informative set of spectra from a number of spectral scans. The denizen transformation is akin to the Householder transformation and inherits its superior numerical properties. The extracted spectra are valuable for library matching of compounds because the extracted spectra are based directly on the spectral data and not some orthogonal projection. The result is a method that is mathematically sound, numerically stable and chemically sensible. The method performs well in speed and analytical results when compared with other currently popular techniques.

In one embodiment of the invention, Y can represent an M×N matrix, denoting the observable intensities of N mass spectra each with M mass-to-charge ratios. These data can be collected from any device that repeatedly scans or samples the mass spectra as it evolves over time or space. In this case, each of the N spectra can represent a scan at a point in time. It is assumed that the N spectra will present themselves such that Y can be expressed as $$Y = XB + \epsilon \qquad (1)$$

where X, an M×K matrix, represents the spectra of K individual compounds with B concentrations. B is a K×N matrix in which the values of each row represent the concentration over the N scans of the compound associated with that row. The concentrations need not follow a known distribution or any kind of calculable function. $\epsilon$ represents uncorrelated noise. Let $\hat{X}$ and $\hat{B}$ represent estimates for X and B respectively.

If the compounds in the sample (and hence their spectra) were already known, X is known and the problem can be reduced to a constrained least-squares calculation to find $\hat{B}$. Likewise, if the concentration profiles were already known, the constrained least-squares procedure could be employed to find $\hat{X}$.

Because the compounds or concentrations are not known, however, the data is used to find K candidate spectra as an initial formulation of $\hat{X}$. It will also become apparent that the algorithm used to select $\hat{X}$ gives reasonable estimates for $\hat{B}$ as well.

The Householder transformation is often employed by the QR algorithm to condition the factor matrix in linear least squares operations. It performs this duty by selecting those columns with the most information and effectively extracts them from the rest of the matrix. This ensures that subsequent selections are linearly independent. The use of a modified Householder transformation is one implementation for the present method because of its ease of operability and its superior numerical properties. The Householder transformation and how it is used in least-squares operations and the QR factorization algorithm is known to those skilled in the art.

Building $\hat{X}$ calls for a similar type of processing. Linearly independent spectra can be selected and extracted from Y in a numerically stable and chemically sensible way. The Householder transformation thus becomes the impetus to develop an analysis method that applies to this situation.

Let the denizen transformation matrix P be an M×M matrix defined as $$P = I - 2 \frac{vv'}{1 + v'v} \qquad (2)$$

with the M length vector v defined as $$v = \frac{x}{\sqrt{x'x}} \qquad (3)$$

where x represents a column vector chosen from one of the columns of Y. When the denizen transformation is applied to a matrix, it has the effect of extracting x from the matrix. The column containing x will be all zeros and the rest of the matrix will be "x free". To keep the values of Y in real-space, values below zero after the transformation are truncated to zero. This is denoted by the $\lfloor \; \rfloor$ symbols. The denizen transformation can be defined as:

$$Den(Y) = \lfloor PY_{\{.,n1 \ldots n2\}} \rfloor \qquad (4)$$

Often it will be desirable to target only specific columns. For example, compounds that elute during a certain time window will reduce the number of columns to be considered. In this case only those columns (n1 . . . n2) will be exposed to the transformation and the rest of Y will remain unchanged.

Note that v in equation (3) differs from the Householder vector by the first term. In fact, if a row of zeros were to be prepended to the top of matrix Y, the two calculations would be the same. This puts the denizen transformation on solid numerical ground and ensures that the roundoff properties associated with the calculations are very favorable.

Extracting $\hat{X}$ From Y

The analysis requires some parameters explained as follows.

Apparatus Noise: This is assumed to be uncorrelated spurious signal that presents itself uniformly throughout Y. This is $\epsilon$ in (1). Since this noise cannot be removed it is basically ignored. It is important to calculate the noise level, however. Spectra will continue to be extracted from Y until the noise level is reached. Most spectra analyzers already truncate signal levels to zero if they fall below some set noise threshold. This threshold is easily measured by finding the smallest non-zero signal level in Y.

Chemical Noise: Y will often contain some persistent signal that is uncorrelated with the compounds being analyzed. This can be caused by a poorly tuned device or some other physical or electronic malfunction. Because the signal is persistent it is easily removed using the denizen transformation as will be explained.

Peak Width: One of the assumptions that allows this method to proceed is that each compound will present itself in a localized region of the data. This region is parameterized as the peak width and can be scaled relative to the intensity of the signal. The methods developed to estimate these noise parameters and elution profiles are beyond the scope of this discussion but are known to those skilled in the art.

One embodiment of the method can be described by the following pseudo-code:

Remove Chemical Noise
given Y return X
calculate spectrum representative of chemical noise
set x=chemical noise
append x onto X
calculate v using (3) and P using (2)
replace Y with Den (Y) using (4) where n1=1 and n2=N Extract Spectra
loop calculate $ss_n = Y'_{.,n} Y_{.,n}$ for $n = 1 \ldots N$ set x = $Y_{\{.,j\}}$ where j indexes max(ss)
append x onto X
calculate peak.width for x
calculate v using (3) and P using (2)
replace Y with Den (Y) using (4) where n1=j−peak.width/2 and n2=j+peak.width/2 until max(ss)<noise An example implementation of the algorithm is illustrated in the following "C" code.

The following is the example code used to calculate v.

```
void eleX_vec(double *x, double *v, int N) {
    int n;
    double norm;
    norm=0;
    for(n=0;n<N;n++) {
        norm += pow(x[n],2);
```

-continued

```
        v[n] = x[n];
    }
    norm = sqrt(norm);
    if(norm > 0) {
        for(n=0;n<N;n++) {
            v[n] /= norm;
        }
    }
}
```

The following is example code that may be used to implement an embodiment of the denizen transform. Notice that an estimate for the corresponding concentration is also calculated as the function proceeds.

```
int eleX_row(double *X, double *w, double *c, double *v, int M,
    int N) {
    int m,n,cnt;
    double beta,dtmp1,dtmp2;
    dtmp1 = 1;
    for(m=0;m<M;m++) {
        dtmp1 += pow(v[m],2);
    }
    beta = 2/dtmp1;
    for(n=0;n<N;n++) {
        w[n] = 0;
        for(m=0;m<M;m++) {
            w[n] += X[n*M+m] * v[m];
        }
        w[n] *= beta;
    }
    cnt=0;
    for(n=0;n<N;n++) {
        c[n] = 0;
        dtmp1 = 0;
        for(m=0;m<M;m++) {
            dtmp2 = v[m] * w[n];
            if(dtmp2 > X[n*M+m]) {
                c[n] += X[n*M+m];
                X[n*M+m] = 0;
            } else {
                c[n] += dtmp2;
                X[n*M+m] -= dtmp2;
                dtmp1 += pow(X[n*M+m],2);
            }
        }
        w[n] = dtmp1;
        if(c[n] > 0) cnt++;
    }
    return(cnt);
}
```

The present method can provide a numerically stable and chemically sensible algorithm that may extract and purify spectra obtained from the detection device. The purified spectra can then be matched against a library for positive identification. This type of processing is important when the physical separation is not complete and the spectra of the individual compounds are confounded. The denizen transformation is introduced as an embodiment of an engine that will propel this method to its destination. The development of the denizen transformation was inspired by the Householder transformation which is at the heart of most linear least-squares operations and has superior numerical properties. This method deals directly with the data to form an orthogonal set of spectra and thus avoids the co-linearity and identifiability problems associated with some machine learning algorithms. The extracted spectra are useful for library matching.

Figure 3:
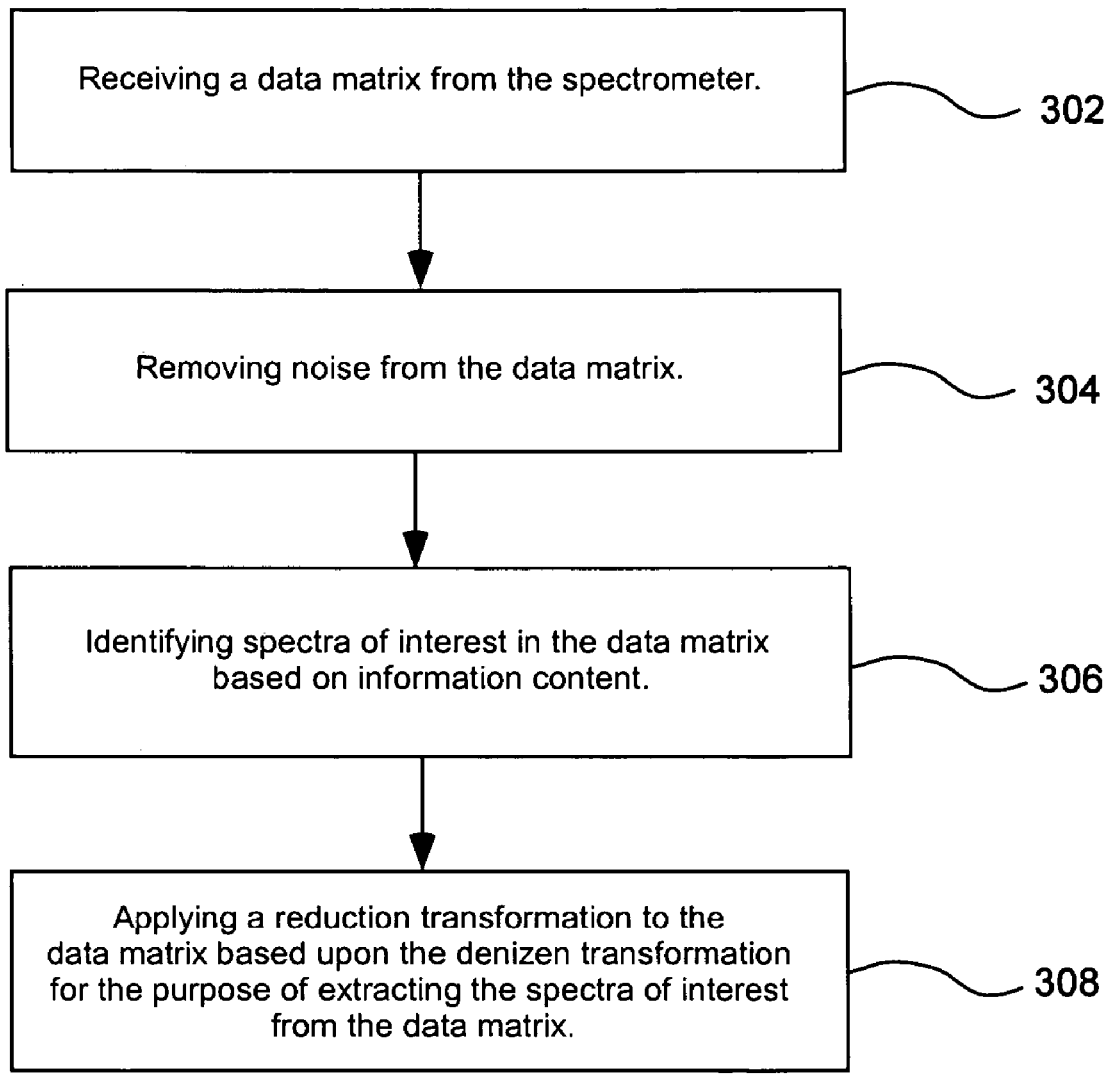
FIG. 3 is a flowchart illustrating an embodiment of a method for extracting spectra from data produced by a spectrometer.

FIG. 3 illustrates a method of extracting spectra from data produced by temporally or spatially indexed spectral scans from a spectrometer. This discussion is a high level overview of the operations of the present system and method. The method can include the operation of receiving a data matrix from the spectrometer, as in block 302. The spectrometer can be a mass spectrometer, an infra-red spectrometer, optical spectrometer, mass spectrometer, an ion mobility spectrometer, or the like.

This data matrix can contain values in rows and the values of each row can represent the concentration of a compound over the N scans of the compound associated with that row. More specifically, the data matrix contains intensity values associated with mass-to-charge ratios. FIG. 1a illustrates an example data matrix produced by a spectrometer showing Chlorobenzene and 4-Hydroxy-4-methyl-2-pentanone. The combined peaks representing compounds can also be seen.

The data will also contain a certain amount of noise from the environment and the spectrometer itself. This noise is measurable and allows the operation of removing noise from the data matrix to be performed, as in block 304.

Next, spectra of interest in the data matrix will be identified based on the information content, as in block 306. The information content that is used as the basis of the selection process for the spectra of interest can be the sum of the squares. In other words, the method will move through the data matrix until the operation of the sum of the squares meets a pre-defined threshold. When the threshold is met, then the selection process is complete. This allows the method to extract spectra that are believed to be relevant to the analysis of the data.

A reduction transformation can then be applied to the data matrix based upon the denizen transformation for the purpose of extracting the spectra of interest from the data matrix, as in block 308. The reduction transformation may be a denizen transform, a modified Householder transformation, or another reduction transformation. Once the spectra of interest have been removed, then it can be verified from the remaining data that the appropriate identified spectra were removed.

Figure 1B:
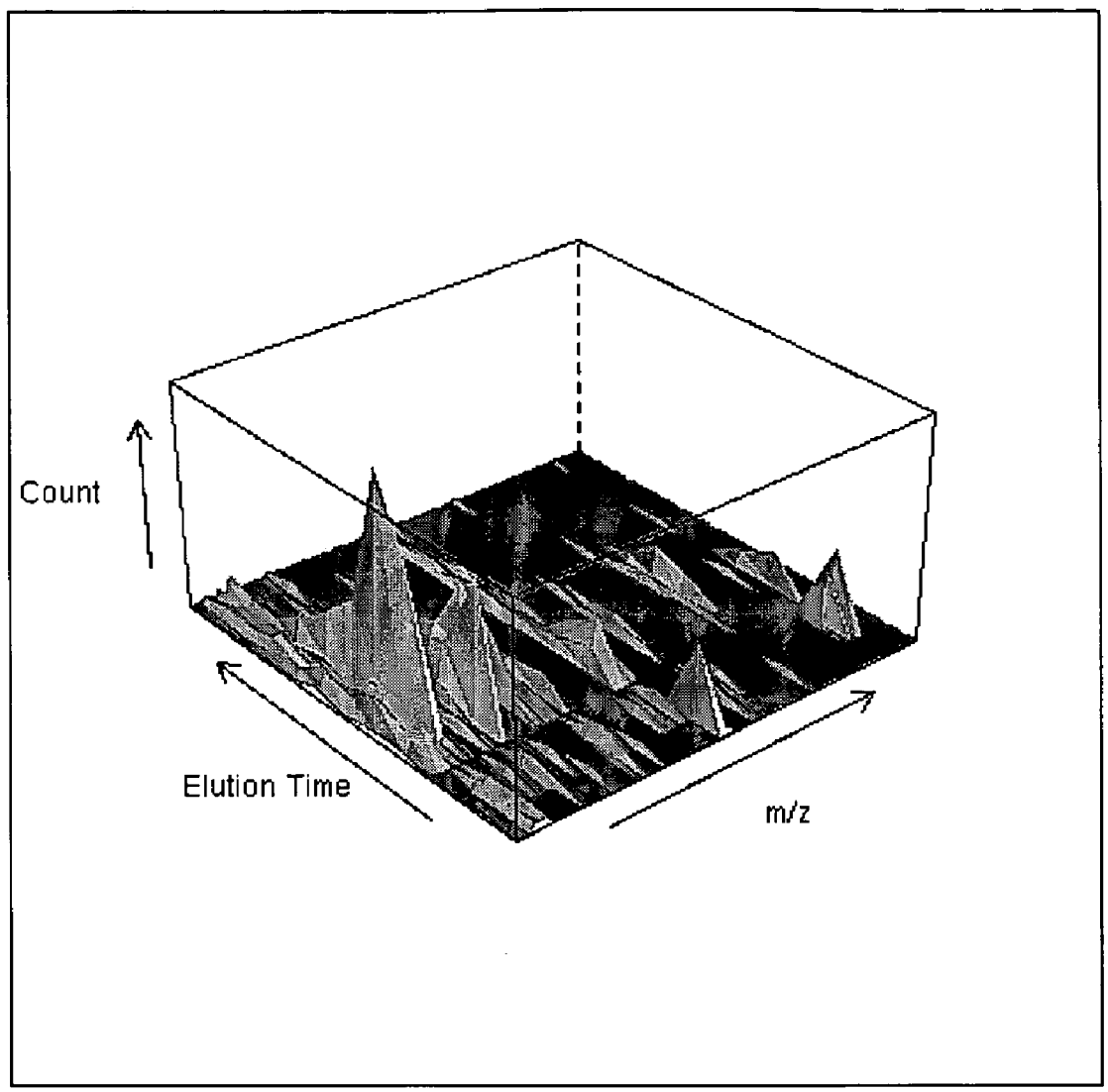
FIG. 1b illustrates an example data matrix as in FIG. 1a with a compound removed from the data matrix in an embodiment of the invention.
Figure 1C:
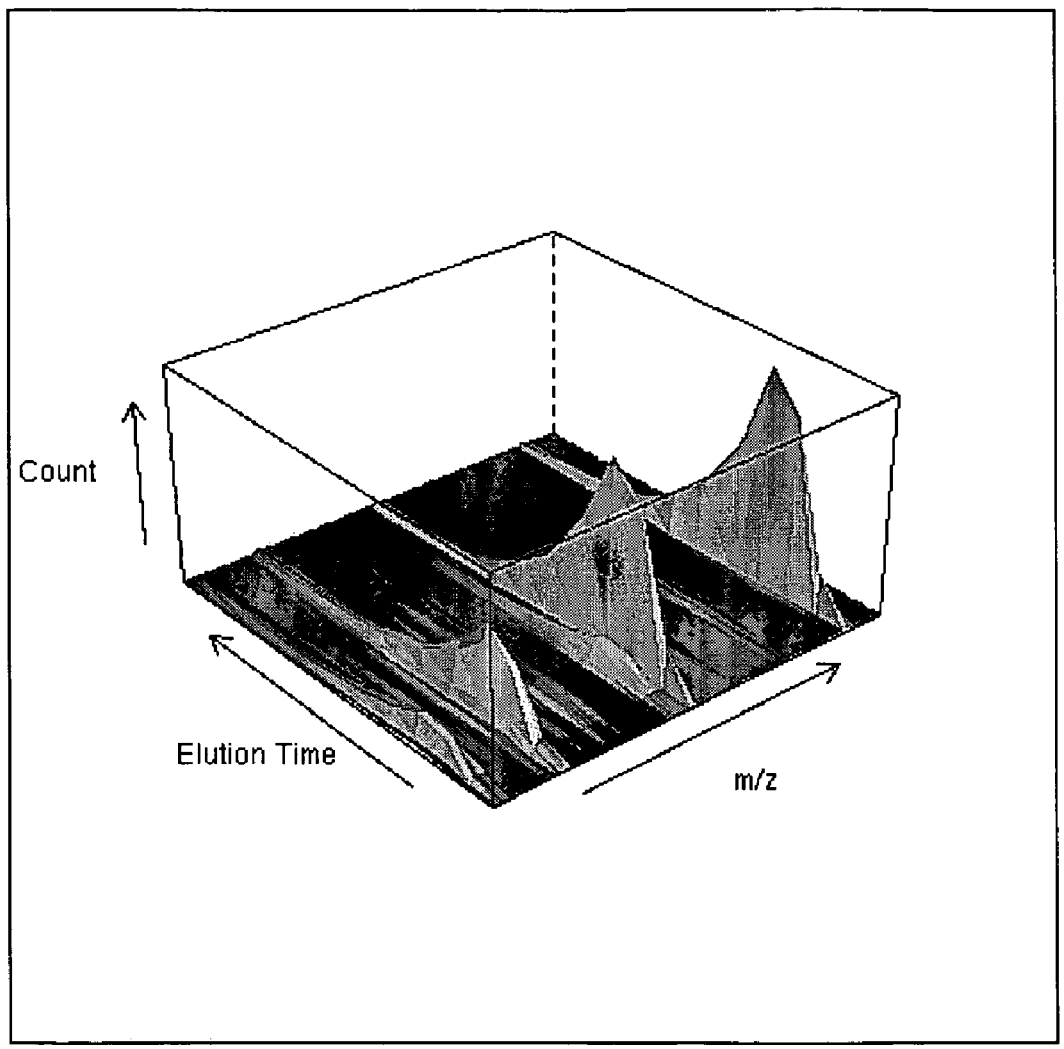
FIG. 1c illustrates an example data matrix of the compound data removed from the original data matrix in an embodiment of the invention.
Figure 2:
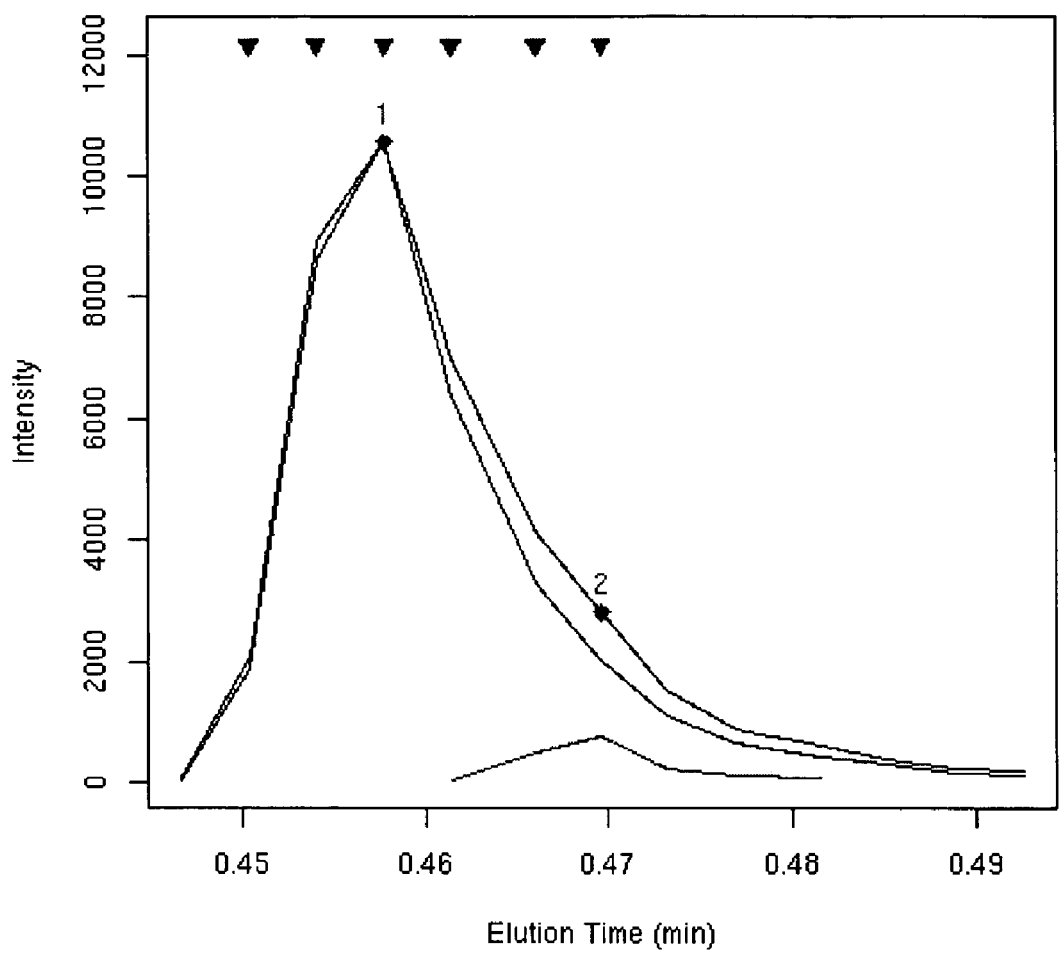
FIG. 2 is a two-dimensional data matrix of the data illustrated in FIG. 1c.

FIG. 1b illustrates an example of a data matrix with the spectra of interest removed. The remaining peaks (displayed in a reduced scale) show the remaining compound data. The spectra of interest was Chlorobenzene which was the column with the largest sum of squares or the most information, and the compound data has been removed. FIG. 1c illustrates the estimated concentration values of Chlorobenzene. In other words, FIG. 1c is an example of the Chlorobenzene spectra once they have been removed. FIG. 2 is a two-dimensional example of the removed Chlorobenzene spectra.

Once the spectra of interest have been removed, the spectra of the same compound that have been removed in different steps can be combined into an aggregate estimate of spectral and concentration values. In other words, the spectra that are believed to be from the same compound can be combined together to form aggregate compound signatures. The compound signatures can be compared against a library of spectral signatures for known compounds. A library can be used of one or more values representing physical properties of compounds combined in a multivariate statistical analysis for the purpose of detection and identification. In addition, hierarchical weighting may be used to identify likely compounds by combining past data and current multivariate statistical analysis of the spectra of interest.

Because the identified signatures have been compressed or combined, the matching of the signatures takes significantly less time than previous library matching systems. This operation allows the system to identify at least one compound and its concentrations in the spectra of interest removed from the data matrix.

This method is also iterative in nature. The reduction transformation can be repeatedly applied to the matrix step in order to extract more spectra of interest from the data matrix. Reductions are applied until the noise floor is reached and at this point it is expected that substantially all of the valuable spectra have been removed from the matrix.

The present invention can also partition the spectra of two or more compounds that were combined in the analysis into various constituent spectral components. This is performed by first sequentially removing the remaining major peaks in the combined spectrum. These extracted spectra can be used as constituent vectors to factor the combined spectrum using constrained least squares. The estimated coefficients of the constrained least squares procedure can be used to determine concentration.

Figure 4:
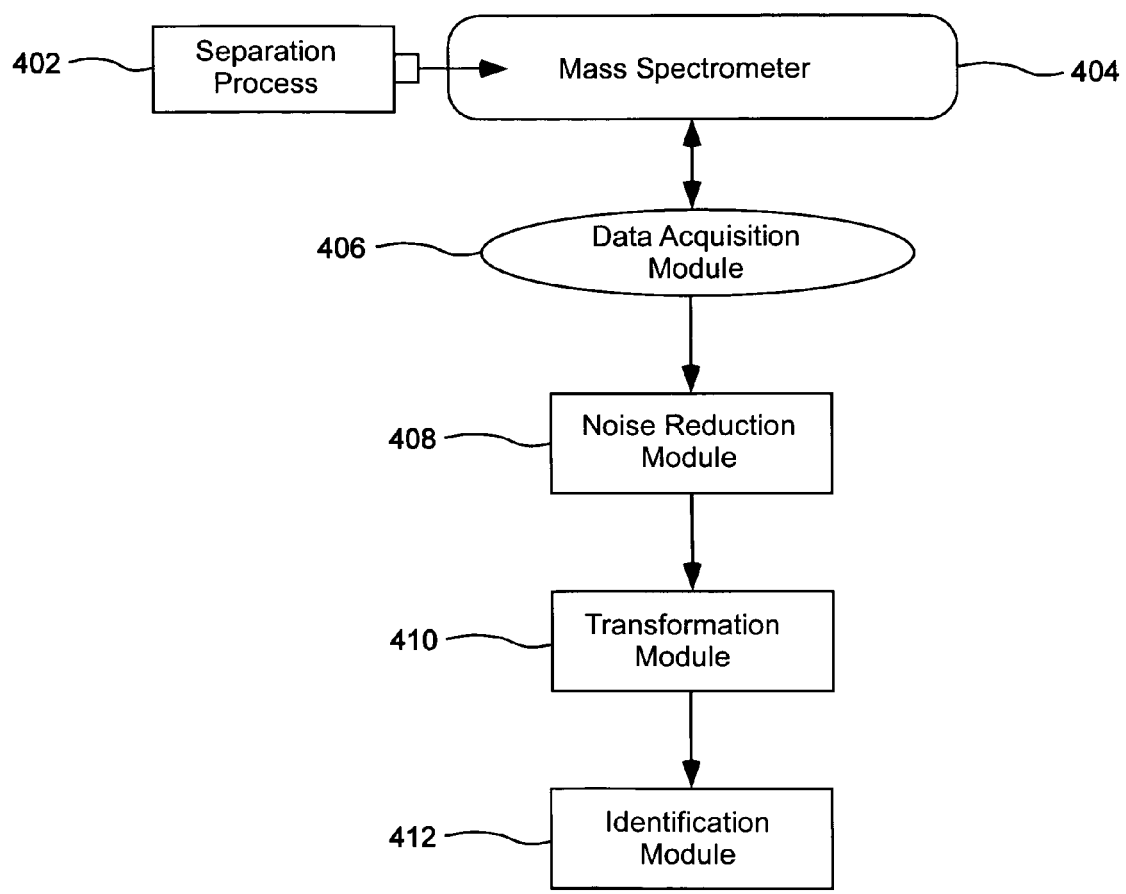
FIG. 4 illustrates a block diagram of an embodiment of a system for spectral analysis.

FIG. 4 illustrates a system for spectral analysis using a mass spectrometer 404 providing intensity values associated with mass-to-charge ratios. The mass spectrometer will be used with a prior separation process 402 which aids in dispersing the ions over time and space. For example, the separation process may be a gas chromatograph, mass spectrometery, electrophoresis, or similar process.

A data acquisition module 406 is configured for receiving a data matrix from a mass spectrometer and the separation process. The data acquisition module is in electronic communication with detection circuitry of the mass spectrometer. For example, a high speed data connection may exist between the two devices.

A noise reduction module 408 is configured to remove noise from the data matrix. As discussed previously some noise will always be present in the current system due to the noise in the electronic components and other environmental noise in the mass spectrometer. The removal of the noise can be performed using known techniques for removing expected amounts of noise.

A transformation module 410 is configured to apply the reduction transformation to the data matrix. This process will be applied using the operations described above to extract spectra data from the data matrix. In addition, an identification module 412 can be configured for identifying spectra of interest in the data matrix. The identification can take place using pattern recognition and a library of compound signatures.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

The invention claimed is:

1. A method of extracting spectra from data produced by temporally indexed spectral scans from a spectrometer, comprising the steps of:
   receiving a data matrix from the spectrometer;
   removing noise from the data matrix;
   identifying spectra of interest in the data matrix based on information content; and
   applying a reduction transformation to the data matrix based upon the denizen transformation for the purpose of extracting the spectra of interest from the data matrix.

2. A method as in claim 1, further comprising the step of testing the spectra of interest to determine whether the identified spectra were removed.

3. A method as in claim 1, wherein the step of identifying spectra of interest in the data matrix based on information content further comprising the step of identifying spectra of interest in the data matrix based on a sum of squares.

4. A method as in claim 2, further comprising the step of identifying at least one compound in the spectra of interest removed from the data matrix.

5. A method as in claim 3, further comprising the step of identifying corresponding amounts of at least one compound in the spectra of interest based on the spectra removed from the data matrix.

6. A method as in claim 5, further comprising the step of comparing a library of mass spectra to the spectra of interest for the purpose of identifying a compound type for the spectra of interest.

7. A method as in claim 5, further comprising the step of using a library of one or more values representing physical properties of compounds combined in a multivariate statistical analysis for the purpose of detection and identification.

8. A method as in claim 3 further comprising the step of using hierarchical weighting to identify likely compounds by combining past data and current multivariate statistical analysis of spectra of interest.

9. A method as in claim 2, further comprising the step of repeating the application of the reduction transformation in order to extract more spectra of interest from the data matrix.

10. A method as in claim 1, wherein the step of receiving a data matrix further comprises the step of receiving intensity values associated with mass-to-charge ratios.

11. A method as in claim 1, further comprising the step of receiving a data matrix from a mass spectrometer that is in communication with a separation process.

12. A method as in claim 1, further comprising the step of combining spectra of the same compound removed in different steps into an aggregate estimate of spectral and concentration values.

13. A method as in claim 1, further comprising the step of partitioning spectra of two or more compounds that were combined in an analysis into various constituent spectral components.

14. A system for spectral analysis using a mass spectrometer providing intensity values associated with mass-to-charge ratios, comprising:
   a data acquisition module configured for receiving a data matrix from the mass spectrometer;
   a noise reduction module configured to remove noise from the data matrix;
   a transformation module configured to apply a reduction transformation based upon the denizen transformation to the data matrix; and
   an identification module configured for identifying spectra of interest in the data matrix.

15. A system as in claim 14, wherein the identification module is configured to identify a compound in the spectra of interest based on mass spectra data removed from the data matrix.

16. A system as in claim 14, wherein the identification module is configured to identify an amount of compound in the spectra of interest based on mass spectra data removed from the data matrix.

17. A system as in claim 14, wherein the transformation module is configured to repeatedly apply the reduction transformation to determine a plurality of compounds that are represented by the spectra of interest.

18. A system as in claim 14, wherein the transformation module is configured to apply a reduction transformation further comprises means for applying a denizen transformation to the spectra of interest.

19. A system as in claim 14, wherein the data acquisition module is configured to receive mass-to-charge ratio data.

20. A method of spectral analysis in a system providing intensity values associated with mass-to-charge ratios, comprising the steps of:
  receiving a data matrix from a mass spectrometer;
  removing noise from the data matrix;
  applying a reduction transformation based upon the denizen transformation to a spectra of interest;
  identifying the spectra of interest in the data matrix;
  storing pattern information reduced with the spectra of interest; and
  comparing the pattern information to a library of mass spectra patterns in order to identify at least one compound captured by the reduction transformation.

21. A method as in claim 20, further comprising the step of repeating the application of the reduction transformation in order to extract at least one spectra of interest from the data matrix.

22. A method as in claim 20, further comprising the step of identifying at least one compound in the spectra of interest based on spectra removed from the data matrix.

23. A method of spectral analysis for mass spectra data from a mass spectrometer, comprising the steps of:
  removing noise from the mass spectra data;
  identifying a spectra of interest in the mass spectra data; and
  applying a denizen transformation to the spectra of interest.

* * * * *